(12) United States Patent
Madsen (10) Patent No.: US 10,376,166 B2
(45) Date of Patent: Aug. 13, 2019

(54) METHOD AND APPARATUS FOR NON-INVASIVE ASSESSMENT OF INTRACRANIAL PRESSURE

(71) Applicant: StatuManu ICP ApS, Glostrup (DK)

(72) Inventor: Jakob Find Munk Madsen, Glostrup (DK)

(73) Assignee: StatuManu ICP ApS, Glostrup (DK)

( * ) Notice: Subject to any disclaimer, the term of this patent is extended or adjusted under 35 U.S.C. 154(b) by 0 days.

(21) Appl. No.: 15/543,300

(22) PCT Filed: Jan. 15, 2016

(86) PCT No.: PCT/EP2016/050785
§ 371 (c)(1),
(2) Date: Jul. 13, 2017

(87) PCT Pub. No.: WO2016/116370
PCT Pub. Date: Jul. 28, 2016

(65) Prior Publication Data
US 2017/0367598 A1    Dec. 28, 2017

(30) Foreign Application Priority Data
Jan. 19, 2015 (DK) .................................. 2015 70027

(51) Int. Cl.
*A61B 5/03* (2006.01)
*A61B 3/12* (2006.01)
(Continued)

(52) U.S. Cl.
CPC ............ *A61B 5/031* (2013.01); *A61B 3/0025* (2013.01); *A61B 3/12* (2013.01); *A61B 3/1241* (2013.01);
(Continued)

(58) Field of Classification Search
CPC ..... A61B 5/031; A61B 3/0025; A61B 5/7278; A61B 5/0816; A61B 5/02416;
(Continued)

(56) References Cited

U.S. PATENT DOCUMENTS

| | | | |
|---|---|---|---|
| 2003/0216650 A1 | 11/2003 | Michelson | |
| 2005/0080336 A1* | 4/2005 | Byrd | ...................... A61B 8/065 600/428 |

(Continued)

FOREIGN PATENT DOCUMENTS

| | | |
|---|---|---|
| CN | 102014731 A | 4/2011 |
| CN | 103536285 A | 1/2014 |

(Continued)

OTHER PUBLICATIONS

Niemeijer, Meindert, Bram van Ginneken, and Michael D. Abramoff. "Automatic determination of the artery vein ratio in retinal images." Medical Imaging 2010: Computer-Aided Diagnosis. vol. 7624. International Society for Optics and Photonics, 2010. (Year: 2010).*

(Continued)

*Primary Examiner* — Amandeep Saini
(74) *Attorney, Agent, or Firm* — Hollard & Hart LLP (57) ABSTRACT

A method for non-invasive assessment of intracranial pressure includes providing an image recording device, recording at least one image of a retina part of an eye of a person using said image recording device, identifying, in said at least one image, at least one artery and at least one vein associated with said artery, determining, in said image, a first characteristic diameter value for said identified artery, determining, in said image, a second characteristic diameter value for said identified vein, calculating an arteriovenous ratio, A/V ratio, based on said first and second characteristic (Continued)

diameter values, and comparing said arteriovenous ratio with a threshold value to estimate intracranial pressure.

9 Claims, 4 Drawing Sheets

(51) Int. Cl.
*A61B 5/02* (2006.01)
*A61B 3/00* (2006.01)
*A61B 3/14* (2006.01)
*A61B 5/024* (2006.01)
*A61B 5/08* (2006.01)
*A61B 5/00* (2006.01)

(52) U.S. Cl.
CPC ............ *A61B 3/14* (2013.01); *A61B 5/02028* (2013.01); *A61B 5/02416* (2013.01); *A61B 5/0816* (2013.01); *A61B 5/7278* (2013.01)

(58) Field of Classification Search
CPC ........... A61B 3/1241; A61B 3/14; A61B 3/12; A61B 5/02028
USPC ........................................................ 382/128
See application file for complete search history.

(56) References Cited

U.S. PATENT DOCUMENTS

| | | |
|---|---|---|
| 2007/0244396 A1 | 10/2007 | Vilser et al. |
| 2010/0234744 A1 | 9/2010 | Kawada |
| 2011/0137182 A1 | 6/2011 | Bellezza |

FOREIGN PATENT DOCUMENTS

| | | | |
|---|---|---|---|
| JP | 10-71125 | 3/1998 | |
| JP | 2000-166876 A2 | 6/2000 | |
| WO | WO 99/18386 | 4/1999 | |
| WO | WO 99/65387 A1 | 12/1999 | |
| WO | WO-9965387 A1 * | 12/1999 | ............... A61B 3/16 |
| WO | WO 02/04564 A2 | 6/2002 | |
| WO | WO 2006/091811 | 8/2006 | |
| WO | WO 2009/126112 | 10/2009 | |
| WO | WO 2012/100221 A1 | 7/2012 | |

OTHER PUBLICATIONS

Meindert Niemeijer et al., Automatic determination of the artery vein ratio in retinal, Proceedings SPIE, vol. 7624, Mar. 4, 2010, 10 pgs.

* cited by examiner

METHOD AND APPARATUS FOR NON-INVASIVE ASSESSMENT OF INTRACRANIAL PRESSURE

BACKGROUND

The present invention relates to a method and an apparatus for non-invasive assessment of intracranial pressure.

The measurement of intracranial pressure (ICP) is an important tool in connection with diagnosing different health disorders, such as head injuries, stroke edema, intracranial hemorrhage, as an overpressure is potentially fatal. Traditionally, the intracranial pressure has been determined by drilling a hole in the skull and inserting a manometer. Needless to say that such an invasive method is potentially dangerous, not only as such, but also indirectly due to risk of infection. Accordingly, various prior art methods for non-invasive measurement of ICP have been proposed, some of which rely on inspection of the optical arteries which supply the eyes with blood. These arteries run from inside the skull to the eyes and are thus influenced by the pressure within the skull.

One type of such non-invasive method is disclosed in WO-A99/18386. In WO-A-99/18386 an ultrasonic transducer is brought into contact with the eye, the eye is put under slight pressure, and the blood velocity is measured in the intracranial and extracranial parts of the artery using Doppler measurement.

Another non-invasive method is disclosed in WO-A-2006/091811. In this method the artery is observed while pressure is increasingly applied to the eye, and it is determined when the artery collapses under the pressure.

Although being non-invasive, these methods involve pressure to the eye which is at best uncomfortable to the patient, but also is not entirely risk-free.

SUMMARY

Based on this prior art it is the object of the present invention to provide a non-invasive method for assessing intracranial pressure (ICP) without the risk and discomfort of the prior art methods.

According to a first aspect of the present invention, this object is achieved by a method for non-invasive assessment of intracranial pressure, said method comprising, providing an image recording device, recording at least one image of a retina part of an eye of a person using said image recording device, identifying, in said at least one image, at least one artery and at least one vein associated with said artery, determining, in said image, a first characteristic diameter value for said identified artery, determining, in said image, a second characteristic diameter value for said identified vein, calculating an arteriovenous ratio (A/V ratio) based on said first and second characteristic diameter values, comparing said arteriovenous ratio with a predetermined threshold value to estimate intracranial pressure.

This allows the assessment of whether there is an abnormally high intracranial pressure that needs to be treated. The treatment itself, however, will depend on the actual cause for the increases intracranial pressure, as diagnosed by a doctor.

According to a second aspect of the present invention the object is achieved by providing an apparatus for performing noninvasive intracranial pressure measurements, said apparatus comprising an image recording device, adapted to record at least one image of a retina part of an eye of a person, an image processing device adapted to identify, in said at least one image, at least one artery and at least one vein associated with said artery, and to determine, in said image, a first characteristic diameter value for said identified artery and a second characteristic diameter value for said identified vein, a data processing device adapted to calculate an arteriovenous ratio based on said first and second characteristic diameter values, and comparing said arteriovenous ratio with a predetermined threshold value, and an output device for outputting information, based on which it can determined whether said predetermined threshold is exceeded or not.

Thereby an apparatus allowing non-invasive assessment of potential intracranial overpressure to be readily performed is provided. This assessment could e.g. be performed by a paramedic at an accident site where a head trauma is suspected.

In this respect it should of course be noted that prior art methods for automatic detection of arteriovenous ratio based on recorded eye images exist, and are described in patent publications, such as WO-A-2012/100221, JP-A-2000-166876 and JP-A-10-71125.

According to a preferred embodiment of the first aspect of the invention, said retina part comprises an optic disc. Scanning the optic disc yields valuable information as to dimensions of the eye and may serve as a reference for determining locations of interest on the veins and arteries.

According to another preferred embodiment of the first aspect of the invention, the method further comprises, recording information about at least one heart pulse cycle of the person, and performing said calculation based on an image recorded at a predetermined time during the pulse cycle of said person. Identifying the time of occurrence of heart beats, where the arteries are subject to increased pressure that is likely to increase the diameter of the arteries, will allow this to be suppressed as a potential error source.

According to a further preferred embodiment of the first aspect of the invention said information about said at least one heart pulse cycle is recorded by recording a number of images of said retina part of the eye of the person using said image recording device. This allows the detection of occurrence of the heartbeats to be performed based on image data from the image recording device alone, in turn, obviation the need for external devices such as electrodes and other devices for recording an electro cardiogram.

According to yet a preferred embodiment of the first aspect of the invention, the method further comprises recording information about at least one respiratory cycle for said person, and performing said calculation based on an image recorded at a predetermined time during the respiratory cycle of said person. Performing, the measurement at a predetermined time during the respiratory cycle allows any changes in intracranial pressure that may arise from respiration, to be suppressed as a potential error source. This, in turn, allows assessment of intracranial pressure to be performed without having to ask a patient to hold his breath. Preferably, the information about the at least one respiratory cycle is recorded by recording a number of images of said retina part of the eye of the person using said image recording device, so as to obviate the need for external devices such as electrodes and other devices for recording an electro cardiogram.

According to a preferred embodiment of the second aspect of the invention, the apparatus further comprises means for determining a heart pulse cycle of the person, and said data processing device is further adapted to take into account temporal information about the heart pulse cycle and the recording of the at least one image, when comparing said arteriovenous ratio with said predetermined threshold value. This allows the detection occurrence of the heartbeats to be performed based on image data from the image recording device alone, in turn, obviation the need for external devices such as electrodes and other devices for recording an electro cardiogram.

According to another preferred embodiment of the second aspect of the invention the apparatus comprises means for determining a respiratory cycle of the patient, and said data processing device is further adapted to take into account temporal information about the respiratory cycle and the recording of the image, when comparing said arteriovenous ratio with said predetermined threshold value. This allows the assessment of intracranial pressure to be performed at a predetermined time during the respiratory cycle where no changes in intracranial pressure are likely to arise from respiration, and thereby to be suppressed as a potential error source. This, in turn, allows assessment of intracranial pressure to be performed without having to ask a patient to hold his breath.

BRIEF DESCRIPTION OF THE DRAWINGS

The present invention will now be described in greater detail based on non-limiting exemplary embodiments, and with reference to the drawings, of which.

DETAILED DESCRIPTION OF THE DRAWINGS

Figure 1:
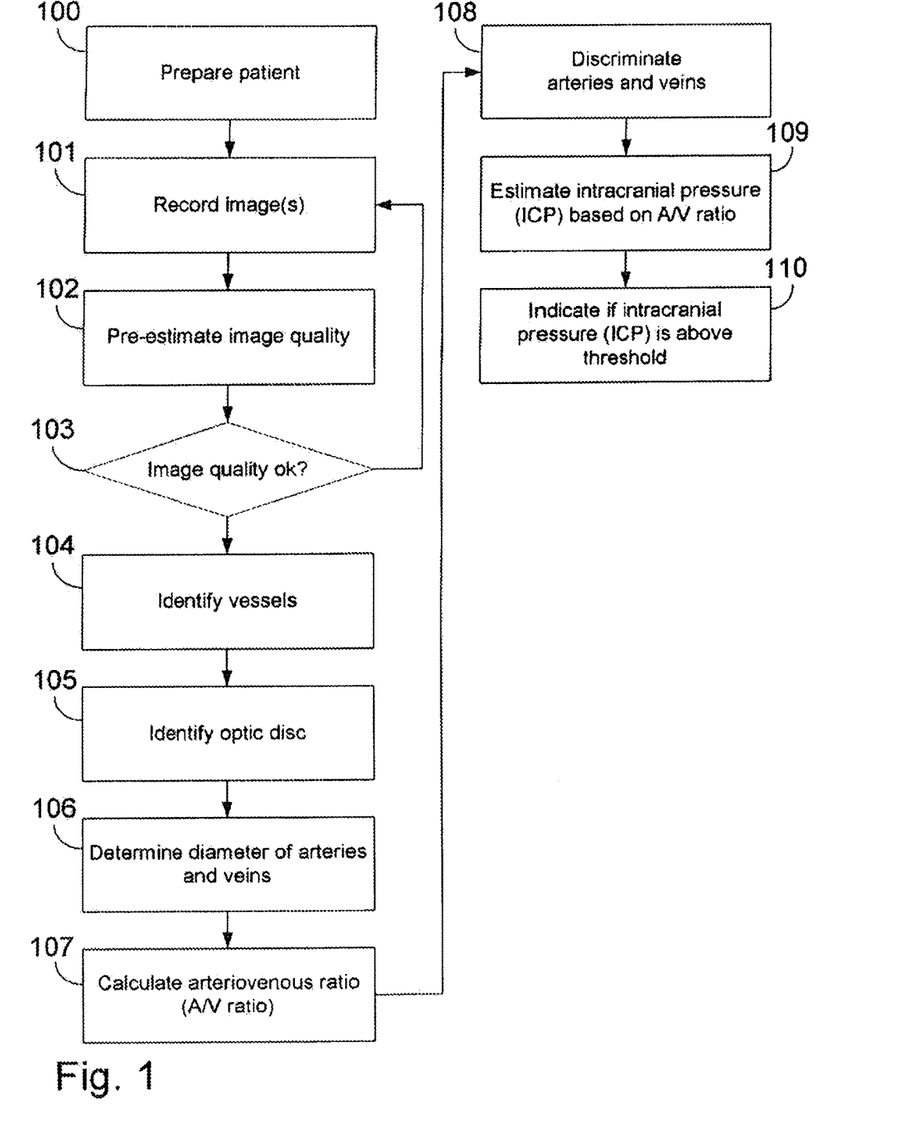
FIG. 1 is a block diagram showing the steps of performing the method according to the invention.

Turning first to the block diagram of FIG. 1, the method according to the invention starts in box 100 with the preparation of the patient, suspected of having increased intracranial pressure (ICP). More specifically it is desirable to dilate the pupil of an eye of the patient in order to record good quality images 1 of the fundus of the eye of the patient. Though the cause for the increased intracranial pressure is not as such diagnosable by the method, a suspected cause and in particular the circumstances may influence the possibilities in dilating the patient's pupil as preparation for the recording of images 1. In particular the possibilities that doctors and nurses have in a hospital environment, may differ from those of ambulance crews, paramedics or the like at an accident site. In a hospital environment there may be time and personnel for chemically dilating the pupil by e.g. dripping the patient's eye with belladonna. This could for instance be the case if the patient is known to suffer from specific conditions, such as hydrocephalus patients, patients with neurosurgical conditions, liver patients, kidney patients, or patients being observed for concussion. If, on the other hand, the patient is a victim of an accident and there is little time available, but an ambulance crew or paramedics suspect a head trauma, such as a developing hematoma, there may only be time for placing the patient in a dark environment, and e.g. ask him to look into the darkness over the shoulder of the person recording the image.

Figure 2:
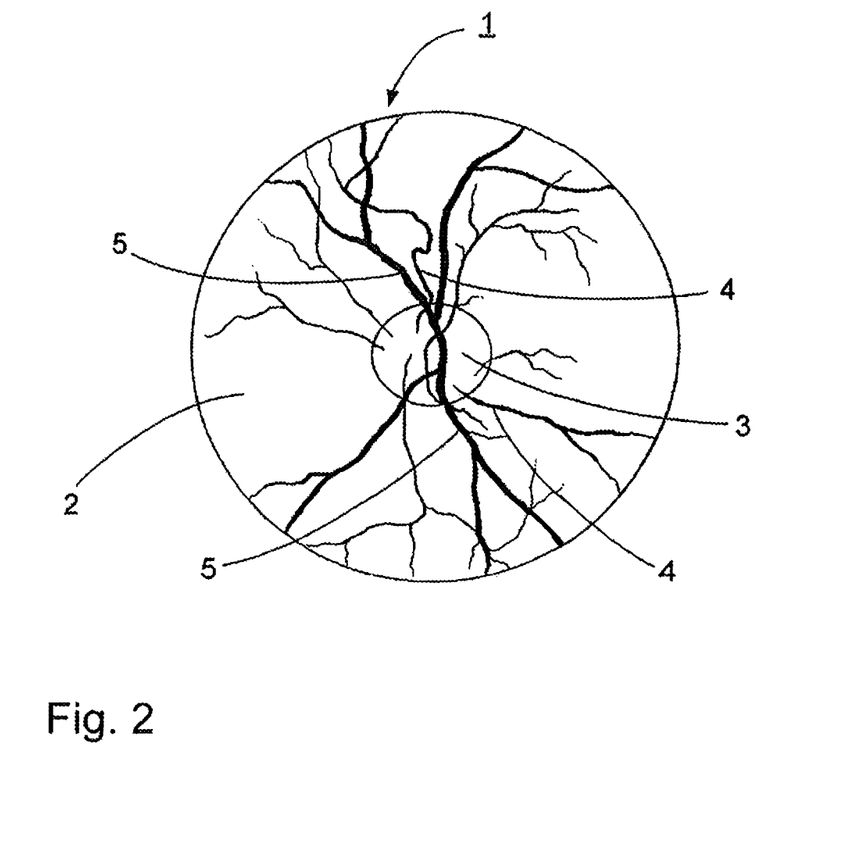
FIG. 2 is a schematic partial image of an eye showing the anatomical features.

Having prepared the patient, the next step is to record, in box 101, one or more images 1 of an eye 8 of the patient. In principle, a single image 1 of the eye 8 will suffice. More specifically the images should be of the fundus 2 of the eye 8 with the optic disc 3 in the middle of which the arteries 4 and veins 5 enter and exit, respectively, along the optic nerve, and from which they branch out in all directions across the fundus 2. As will be explained later it may be advantageous to record a plurality of sequential images 1 over a certain time interval, in order to minimize error sources, but in principle a single image 1 of good quality, mainly a sharp image 1, suffices.

Figure 4:
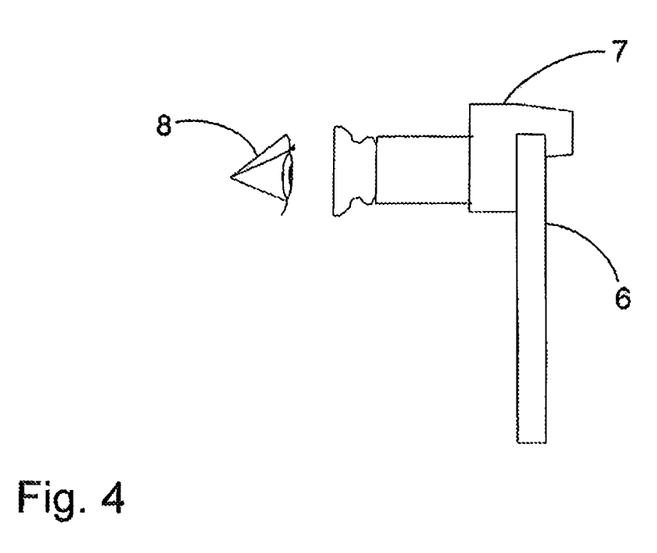
FIG. 4 is a schematic drawing illustration an apparatus for performing the method according to the invention.

In principle, the image 1 may be recorded using any suitable device. This could be a dedicated device for this specific purpose. It could also be a digital camera with suitable optics, preferably in combination with a data processing device, such as a personal computer, PC, for inter alia processing the image data according to the method, and possibly providing storage capacity for the recorded images 1, at least temporarily. In particular, however, the image recording device could be the built in camera of a smart phone 6 fitted with a suitable lens adapter 7, as illustrated in FIG. 4. The smart phone 6 could thus be used both for the recording of the images 1, and the subsequent image data processing according to the method, as well as providing storage capacity for the recorded images 1. Suitable lens adapters 7 for recording eye images 1 are commercially available, such as the iExaminer™, from Welch Allyn, Inc., 4341 State Road, Skaneateles Falls, N.Y. 13153, USA. In general, but particular when using a smart phone 6 as the image recording device, it should be noted that the image recording device should record the images 1 in an uncompressed format, such as Bitmap (.bmp), Tagged Image File (.tiff), JPEG2000 in lossless setting (.JP2, .JPF, .JPX). Compression may blur images 1 and therefore adversely affect the subsequent image data processing of the method according to the invention, and is therefore not desirable.

To ensure the quality of the images 1, an image quality pre-estimate is, in box 102, performed in order to establish whether images 1 are sharp. This can be done by classifying areas in the images 1. A normal image 1 will comprise different areas and features. More specifically, in a recorded image 1 of an eye 8 there will typically be overexposed areas, underexposed areas, background areas of the fundus 2, the optic disc 3, and blood vessels, i.e. veins 4 and arteries 5. If the image 1 is sharp transitions will be readily identifiable. This may be done by a person visually inspecting the image 1, but according the invention this is preferably performed in an automated process by image processing software, running on the dedicated device, on the associated computer, or on the smart phone 6. The preferred way of doing this is to use an edge filtering method that leaves an edge filtered image showing edges only. This is one of the reasons why compressed images 1 are unwanted, as obviously the desire is to have sharp edges of transitions in the images 1, not artificially blurred by compression. For the same reason any automatic filtering and edge enhancement in the camera should be disposed of, suppressed or otherwise avoided. This is in particular the case if the camera is the built-in camera of a smart phone 6, where such features are commonplace.

Mean filtering is then applied to the edge filtered image. In the mean filtering, the edge filtered image is broken down in blocks of e.g. 50×50 pixels. In these blocks the image processing software determines the frequency of edges within each of the blocks. The image can then be classified according to the distribution between blocks having a low frequency of edges and blocks having a high frequency of edges. If the recorded image 1 is blurred the edge filtered images 1 will yield very few or no blocks with a high frequency of edges, and can therefore, in box 103, be rejected by the image processing software. Consequently, the method returns to, box 101, where a new image 1 recorded. A pre-estimate is then performed on the new image 1 in box 102, and this process repeated as often as necessary until an image 1 is accepted in box 103.

Having determined that the quality of the recorded image 1 is appropriate, the vessels are, in box 104, identified among the other features of recorded image 1. Like the image quality pre-estimation, this identification of vessels may also be done by a person visually inspecting the image 1. However, according the invention the identification is preferably performed in an automated process by the image processing software, running on the dedicated device, on the associated computer, or on the smart phone 6.

The identification of the vessels among the other features may be performed in various ways, based on known image analysis methods, or by visual inspection of an image 1. A person will normally not have problems identifying blood vessels in the recorded images 1. Different areas of the image 1 have already been determined in the pre-estimate of the image quality, and areas identified by the person as blood vessels, may simply be marked by mouse click or similar, when the person views the recorded image 1 on a display. However, since a fully automated method that can be implemented in a device is desired, it is currently preferred to use Gauss line analysis. Gauss line analysis is well known, and implemented in existing image processing software, such as Halcon 12 from MVTec Software GmbH.

The Gauss line analysis can be fully automated and performed by the imaging processing software to find lines in images 1. It should be noted that the term lines is not to be understand in a narrow mathematical sense as one-dimensional straight lines, but is to be understand lines with a certain width, as well as curves and other features. The width corresponds to the diameter of the blood vessel which the method eventually needs to determine in order to calculate the A/V ratio. Because there are both arteries 4 and veins and both of these types of blood vessels are branched, line segments with more or less constant widths rather than continuous lines will be identified. The Gauss line analysis yields the width at each point along all these line segments. The Gauss line analysis, however, will not discriminate between arteries 4 and veins, and this will have to be performed in a separate step.

As a first alternative to Gauss line analysis, a texture analysis with subsequent discriminant analysis, as described in WO-2006/042543, could be used to identify major and minor blood vessels and other features, such as fundus 2, the optic disc 3, out of image areas, edges between e.g. optic disc 3 and fundus 2, etc. It is thus to be understood that the identification of the optic disc 3, in box 104, need not be performed as a separate subsequent step of the method according to the invention. In addition to texture, other parameters, mean values of colours (R, G, B), and variance of colours (R, G, B) may be used to convert the image data to classes. This texture analysis itself will, however, not yield any discrimination between arteries 4 and veins, and this will still have to be performed in a separate step.

A second alternative would be manual selection, in box 104, by a person visually inspecting the image 1 on a screen, and making blood vessels using a suitable maker known per se, such as a computer mouse and pointer, a stylus on a touch screen or the like.

More alternatives exist and in fact the libraries of the Halcon 12 software comprise a number of preprogrammed software algorithms for blood vessel detection.

The efficiency and reliability of the various image processing methods for finding the blood vessels in an image 1 may depend on the actual image 1, or the quality thereof. That is to say, one method may provide a reliable result when used on one image 1, and a less reliable result, such as an ambiguous result, or even fail entirely, when used on another image 1. It is therefore preferred to subject each image 1 to several of the available image analysis methods, and combine the results for increased reliability.

Having identified the vessels this way, the optic disc 3 could, in box 105, be identified in as similar manner using the marker. The optic disc 3 is quite easily distinguishable, because it is much brighter than the fundus 2 as such. Evidently, in this case the order of boxes 104 and 105 of the diagram of FIG. 1 could be swapped, i.e. the optic disc 3 being identified first and the vessels second.

Because the optic disc 3 is much brighter than the rest of the fundus 2, identifying it is also quite easily distinguished in an automated process using image processing software.

In a first alternative, the optic disc 3, or at least a representative location thereof, could be identified based on the vessels, which all enter the eye 8 along the optical nerve at the centre of the optic disc 3.

In a second alternative, the optic disc 3 may be found by shape search by the image processing software.

In a third alternative the optic disc 3 may be found by image correlation where the image processing software searches for the best correlation in the image 1 with an image of a circular disc.

As with the identification of the blood vessels, several different image processing methods could be used on each image 1 and a combined result be used.

In the process of identifying the vessels an experienced person would at the same time be able to discriminate between veins 5 and arteries 4, and identify pairs of corresponding arteries 4 and veins 5. In doing so there are a few general rules that are helpful, not only in the visual inspection, but also in any automated process. The largest pair of veins 5 and arteries 4 in the image 1 would in most persons extend in a generally vertical direction upward from the centre optic disc 3 where veins 5 arteries 4 enter the eye 8 along the optical nerve and second largest pair would extend downward from the centre of the optic disc 3. This a general rule and there are individual differences between persons and exceptions. In respective pairs of veins 5 and arteries 4 the veins 5 will generally have a larger diameter than the arteries 4 and thus be wider in an image 1. Both arteries 4 and veins 5 branch out in a somewhat fan shaped manner, meaning the artery vessels do not cross each other in the image 1, and vein vessels do not cross each other in the image 1. Thus, if vessels cross, one must be an artery 4 and the other a vein 5 or vice versa. As for the major veins 5 and arteries 4 extending in the vertical direction upwardly and downwardly from the centre of the optic disc 3 above and below the centre of the optic disc 3, the will generally be relatively close to each other over at least one segment and readily identifiable as a pair.

For an automated system, however, it is convenient to start with the fact that a vein 5 generally has a larger diameter than its corresponding artery 4. Accordingly, diameters of vessels are, in box 106, determined at one or more distances from the centre of the optic disc 3 (or alternatively from a point at the optic nerve at which veins 5 and arteries 4 generally converge.

Based on the determined vessel diameters for veins 5 arteries 4 the diameter ratio(s) at given distances from the optic disc 3 can be calculated. Some of these ratios will be A/V ratios, as indicated in box 107. Others will be false results such as A/A ratios, V/V ratios, and V/A ratios, and some of these may be from non-matching pairs of veins 5 and arteries 4.

However, for discriminating between veins 5 and arteries 4, as indicated in box 108, a simple evaluation of the ratio will often suffice. If the ratio is too close to 1.0, then both vessels are likely to be either veins 5 or arteries 4, if the ratio is too far above or below 1.0 then the vessels are not likely to be a matching pair. If the ratio is suitably above 1.0 then the result is likely to be a V/A ratio of a matching pair, as veins 5 generally have larger diameters than arteries 4. In that case the reciprocal value will yield the desired A/V ratio. If the ratio is suitably below 1.0 and suitably above 0.0 then the result is likely to be a useful A/V ratio. When repeated for a suitable number of locations in the image 1 a statistical analysis may be made on the likely matching pairs, yielding a suitable A/V ratio.

If a number of sequential images 1 are taken within a short period of time, such as one or two seconds, and the A/V ratio determined, preferably recorded at same locations, in the sequential images 1, the identification of veins 5 and arteries 4 can be verified because veins 5 and arteries 4 respond differently to the pressure changes during a heart beat cycle, causing the A/V ratio to vary in a characteristic manner over time. Present day cameras, and even standard smart phone cameras function very well as high speed cameras with up to 30 images per second, giving a sufficient number of images 1 to identify these A/V ratio changes. High end smart phones such as iPhone 6 are even capable of recording 240 images per second, which is far more than needed for this purpose. Moreover, if the finally determined A/V ratio is based on a median value from all points in all images 1, rather than a mean value, the changes on the A/V ratio from the heartbeat may be negligible.

The statistical normal distribution of the A/V ratio in people with normal intracranial pressure is generally known for the population, and the determined A/V ratio can therefore be compared to that statistical normal distribution. The inventor has found that an intracranial overpressure is the single most influential factor on the A/V ratio in the eye 8, by far outweighing other factors such as intake of alcohol, nicotine and other drugs, high blood pressure, pulse and respiration. Thus, by comparing, in box 109, the A/V ratio to the known statistical normal distribution an indication or alert to potential intracranial overpressure above a given threshold can be given, in box 110, if the finally determined A/V ratio is below a given threshold, e.g. in a predetermined lower percentile of the normal distribution of the general population. The alert could be acoustic or visual, e.g. in text format on a display of the apparatus in which the method according to the invention is implemented, e.g. on the display of the smart phone 6.

As to the other factors, taking images 1 over a longer time spans such as 10-15 would suffice to comprise at least one respiratory cycle which may readily be identified, and excluded as an error source in a manner similar to the heartbeat.

Figure 3A:
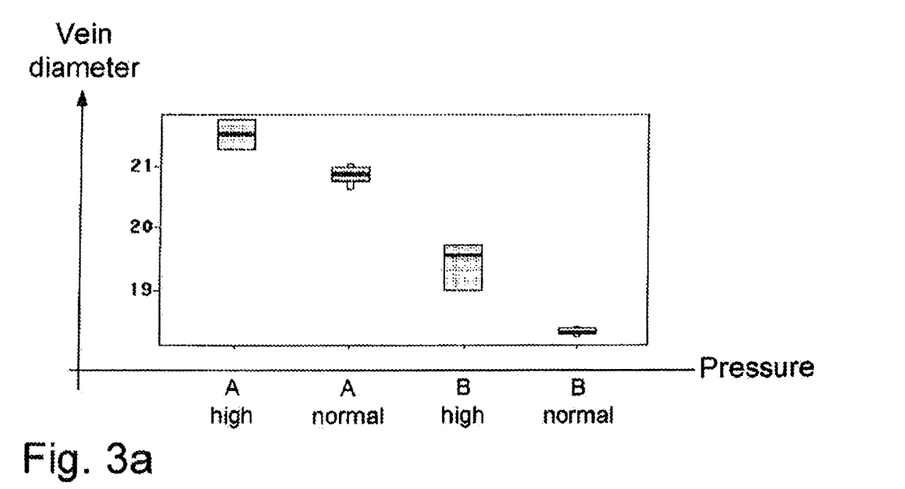
FIGS. 3a and 3b show experimental data of vein and artery diameters at different intracranial pressures of two test subjects performing a Valsalva maneuver.
Figure 3B:
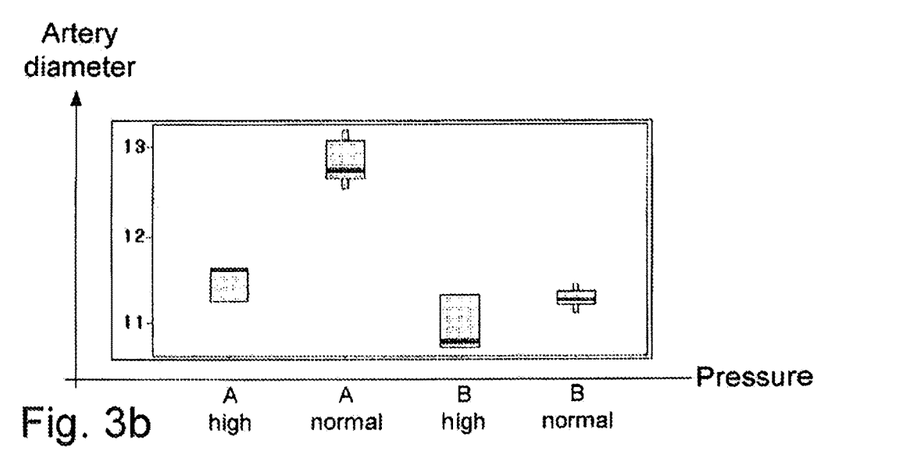

Turning now to FIGS. 3a and 3b, test results showing changes in vein and artery diameters for two test subjects, A and B, performing a number of Valsalva maneuvers are depicted. A number of pictures have been analyzed causing some deviation in the detected artery and vein diameters from the median value indicated with the horizontal bars.

FIG. 3a shows the vein diameters for the two test subjects, respectively when normal intracranial pressure exists, and when high intracranial pressure due to exists due to the test subjects performing of the Valsalva maneuvers. As can be seen, the vein diameter increases with increased pressure for both test subjects. It will be noted that the increase is more pronounced for test subject B than for test subject A.

Similarly FIG. 3b shows the artery diameters significantly for the two test subjects, respectively when normal intracranial pressure exists, and when high intracranial pressure due to exists due to the Valsalva maneuvers. As will be noted the artery diameters decrease, rather than increase, with increased intracranial pressure. It will also be noted that the decrease is more pronounced in test subject A than in test subject B.

However, irrespective of the fact that the increase of vein diameter is more pronounced for test subject B, and the decrease of artery decrease is more pronounced for test subject A, the resulting A/V ratios turn out substantially the same for both. More specifically, for both test subjects the A/V ratios calculated based on the median values, turn out to be approximately 0.54 for the high pressure situation, and approximately 0.61 for the low pressure situation. This is a significant difference that will readily be distinguishable from normal values in the normal distribution among the general population, which will not all have the same normal A/V ratios 0.61 which the test subjects happen to share.

Irrespective of this, getting an alert to potential intracranial overpressure is, however, not always sufficient. First of all there will evidently be people with a fully normal A/V ratio in the lower percentile, which will give false positives. Secondly, in some cases such as e.g. a head injury in a traffic accident, intracranial overpressure may not have developed at the time the ambulance or paramedics arrive, as the intracranial overpressure needs time to evolve.

The A/V ratio measurement according to the method described above is therefore preferably performed one or more times later, say after arrival in the hospital, and hours later during monitoring. The method according to the invention is particularly suitable for this, as compared to prior art method, because it is non-invasive and hardly provides any discomfort for the patient. For the same reason the present invention renders itself suitable for monitoring other patients, e.g. chronic patients with diagnosed diseases such as such as hydrocephalus patients, patients with neurosurgical conditions, liver patients, kidney patients. Such patients may be monitored by recording and monitoring A/V ratio at regular intervals, such as once, twice or three times a day. In this way it can be determined whether the intracranial pressure is rising or not, and accordingly whether a potentially lethal intracranial pressure is likely to evolve.

The skilled person will realize that even though in the above description of exemplary preferred embodiments, reference is made to embodiments where the method is inter alia implemented in software executed on a smart phone with a suitable lens adapter, numerous other variants and implementations will be possible within the scope of the claims. In particular, it is believed that smart phones may already exist on the market, having sufficient imaging qualities to obviate the need for a lens adapter. Finding such phones would require no inventive skill. Also, the skilled person will realize that in case of lack of computing power, data may be uploaded from the smart phone to a remote processing and storing site, from which the resulting information about an alert could be downloaded.

What is claimed is:

1. A method for non-invasive assessment of intracranial pressure, said method comprising,
   providing an image recording device, recording at least one image of a retina part of an eye of a person using said image recording device, identifying, in said at least one image, at least one artery and at least one vein associated with said artery, determining, in said image, a first characteristic diameter value for said identified artery, determining, in said image, a second characteristic diameter value for said identified vein, calculating an arteriovenous ratio based on said first and second characteristic diameter values, and outputting an assessment of said intracranial pressure based on comparing said arteriovenous ratio with a threshold value.

2. The method according to claim 1, wherein said retina part comprises an optic disc.

3. The method according to claim 1, further comprising, recording information about at least one heart pulse cycle of the person using said image recording device, and performing said calculation based on an image recorded at a predetermined time during the pulse cycle of said person.

4. The method according to claim 3, wherein said information about said at least one heart pulse cycle is recorded by recording a number of images of said retina part of the eye of the person using said image recording device.

5. The method according to claim 1, further comprising recording information about at least one respiratory cycle for said person, and performing said calculation based on an image recorded at a predetermined time during the respiratory cycle of said person.

6. The method according to claim 5, wherein said information about at least one respiratory cycle is recorded by recording at least one image of said retina part of the eye of the person using said image recording device.

7. An apparatus for performing noninvasive intracranial pressure measurements, said apparatus comprising an image recording device, adapted to record at least one image of a retina part of an eye of a person, an image processing device adapted to identify, in said at least one image, at least one artery and at least one vein associated with said artery, and to determine, in said image, a first characteristic diameter value for said identified artery and a second characteristic diameter value for said identified vein, a data processing device adapted to calculate an arteriovenous ratio based on said first and second characteristic diameter values, and comparing said arteriovenous ratio with a predetermined threshold value, and an output device for outputting intracranial pressure information indicating whether said predetermined threshold is exceeded or not.

8. The apparatus according to claim 7, further comprising means for determining a heart pulse cycle of the person, and wherein said data processing device is further adapted to take into account temporal information about the heart pulse cycle and the recording of the at least one image, when comparing said arteriovenous ratio with said predetermined threshold value.

9. The apparatus according to claim 7, further comprising means for determining a respiratory cycle of the patient, and wherein said data processing device is further adapted to take into account temporal information about the respiratory cycle and the recording of the image, when comparing said arteriovenous ratio with said predetermined threshold value.

* * * * *